US012691272B2

(12) United States Patent
Glowczwski

(10) Patent No.: US 12,691,272 B2
(45) Date of Patent: Jul. 28, 2026

(54) VASCULAR ACCESS DEVICE WITH VESSEL ACCOMODATION

(71) Applicant: VOYAGER BIOMEDICAL, INC., Houston, TX (US)

(72) Inventor: Alan Glowczwski, College Station, TX (US)

(73) Assignee: VOYAGER BIOMEDICAL, INC., Houston, TX (US)

( * ) Notice: Subject to any disclaimer, the term of this patent is extended or adjusted under 35 U.S.C. 154(b) by 569 days.

(21) Appl. No.: 18/037,703

(22) PCT Filed: Nov. 19, 2021

(86) PCT No.: PCT/US2021/060069
§ 371 (c)(1),
(2) Date: May 18, 2023

(87) PCT Pub. No.: WO2022/109255
PCT Pub. Date: May 27, 2022

(65) Prior Publication Data
US 2024/0001098 A1     Jan. 4, 2024

Related U.S. Application Data

(60) Provisional application No. 63/115,981, filed on Nov. 19, 2020.

(51) Int. Cl.
*A61M 39/02* (2006.01)
*A61M 1/36* (2006.01)

(52) U.S. Cl.
CPC ...... *A61M 39/0208* (2013.01); *A61M 1/3655* (2013.01); *A61M 2039/022* (2013.01); *A61M 2039/0226* (2013.01)

(58) Field of Classification Search
CPC ............ A61M 1/3655; A61M 39/0208; A61M 2039/022; A61M 2039/0226
See application file for complete search history.

(56) References Cited

U.S. PATENT DOCUMENTS

2013/0012890 A1     1/2013   Glenn
2013/0072883 A1     3/2013   Edoga et al.
(Continued)

FOREIGN PATENT DOCUMENTS

WO        2006116188 A2     11/2006
WO        2021067885 A1      4/2021

OTHER PUBLICATIONS

International Search Report and Written Opinion issued in International Application No. PCT/US2021/060069, mailed Feb. 8, 2022, 8 pages.
(Continued)

*Primary Examiner* — John Kim
(74) *Attorney, Agent, or Firm* — Talem IP Law, LLP

(57)                 ABSTRACT
A vascular access device with vessel accommodation includes a top portion and a bottom portion. The top portion includes a top vascular housing for encasing a top portion of a vessel when implanted and at least one hollow male member extending from the top vascular housing. The bottom portion includes a bottom vascular housing for encasing a bottom portion of the vessel when implanted and at least one female member disposed at an upward-facing coupling edge of the bottom vascular housing. The at least one female member receives the at least one hollow male member of the top portion to couple the top portion and the bottom portion together such that the top and bottom portions can move vertically with respect to one another but rotation and movement in the horizontal/longitudinal directions are inhibited.

29 Claims, 12 Drawing Sheets

(56)                    References Cited

U.S. PATENT DOCUMENTS

| 2017/0368324 | A1 | 12/2017 | Glowczwski et al. |
| 2019/0269842 | A1 | 9/2019 | Young et al. |

OTHER PUBLICATIONS

Extended European Search Report issued in European Application No. 21895659.7, mailed Sep. 16, 2024, 8 pages.

400

404   403                                                                           405    408

406

VASCULAR ACCESS DEVICE WITH VESSEL ACCOMODATION

CROSS-REFERENCE TO RELATED APPLICATIONS

This application is the U.S. National Stage Application of International Application No. PCT/US2021/060069, filed Nov. 19, 2021, which claims the benefit of U.S. Provisional Patent Application Ser. No. 63/115,981, filed Nov. 19, 2020, which are hereby incorporated by reference in their entirety.

BACKGROUND

Every year, millions of people in the United States and around the world require access to vessels for medical treatment, such as dialysis, chemotherapy, drug delivery, or diagnostic procedures (e.g., monitoring levels of components in the blood). Dialysis removes waste, salt, and excess water from the blood to prevent a toxic build-up in the body. Dialysis also helps to maintain a safe level of chemicals in the blood (e.g., potassium, sodium, and bicarbonate) as well as help control the person's blood pressure. Approximately half a million Americans are on dialysis alone. Chemotherapy is used to treat cancers by attacking the fast-growing cells associated with the cancer. Chemotherapy and other drug delivery may involve repeated access to vessels over time for medical treatment.

Patients may need increased blood flow through a vessel, in which case a connection can be created between an artery and the vessel to create an arteriovenous fistula (AVF). As an example, dialysis patients require two needles to be inserted into a vessel, three times a week, in order to get life-saving medical treatment. Indeed, repeated punctures to the vessel (e.g., 200+ punctures per year) can contribute to the collapse of the vessel, which generally happens over time and therefore requires more and more painful punctures to allow for satisfactory access to the vessel as time passes. Poor punctures in which the needle misses and/or damages more of the vessel than needs to be damaged to access the blood expedites the collapse of the vessel. If/when the vessel collapses, an interventional radiologist can perform an angioplasty to attempt to recover the vessel, however, recovery of the vessel is not always possible (e.g., when the vessel is too damaged to recover). If an angioplasty is not possible, the patient is left with the unenviable choice of either having another invasive surgery or risking death without dialysis, due to the decreased effectiveness of medical treatment due to the use of the collapsed vessel.

BRIEF SUMMARY

Vascular access devices are described. A vascular access device with vessel accommodation can facilitate recovery and prevention of collapsed and damaged vessels. Advantageously, the described vascular access devices with vessel accommodation can help prevent damage to a vessel (including those supported by an AVF) as well as recover that vessel if/when that vessel is damaged and/or collapsed, therefore preventing or at least minimizing the likelihood of invasive and redundant surgeries. Furthermore, the described vascular access devices can also be placed around already collapsed portions of the vessel, making angioplasty easier and/or making recovery of a vessel that would otherwise be too damaged for an angioplasty recoverable.

A vascular access device with vessel accommodation is configured such that movement in linear horizontal and longitudinal directions, rotation around the horizontal and longitudinal axes, and rotation around the vertical axis may all be inhibited while the top and bottom portions of the vascular access device are able to move with respect to each other (e.g., separate and return) in a linear vertical direction (e.g., when an interventional radiologist performs an angioplasty on the portion of the vessel that is encased by the vascular access device). In some cases, additional features are provided that also minimize the likelihood of having a damaged and/or collapsed vessel in the first place, including damage that may otherwise be caused by the vascular access device itself.

According to various implementations, a vascular access device with vessel accommodation includes a top portion and a bottom portion. The top portion includes a vascular access aperture and a at least one male/female member. The bottom portion includes at least one mating member corresponding the to the at least one male/female member of the top portion that allows for controlled movement of the top portion and the bottom portion to accommodate enlarging vessels.

The top portion includes a top vascular housing for encasing a top portion of a vessel (proximal to a surface of a patient's skin) when implanted. The bottom portion includes a bottom vascular housing for encasing a bottom portion of the vessel (distal to the surface of the patient's skin) when implanted. The top portion and the bottom portion, when coupled together and affixed to tissue surrounding the vessel, are configured to permit movement with respect to each other in the linear vertical direction while preventing movement in the linear horizontal and longitudinal directions and rotational movement.

In one implementation, the at least one male/female member of the top portion includes at least one hollow male member extending from a side of the top vascular housing. Each of the at least one hollow male member includes a slot exposing an interior surface of the at least one hollow male member and a top aperture formed within a downward-facing coupling edge positioned proximal to a bottom surface of the top vascular housing. In this implementation, the at least one mating member of the bottom portion includes at least one female member disposed at an upward-facing coupling edge of the bottom vascular housing. The at least one female member includes a bottom aperture for receiving the at least one hollow male member of the top portion.

In another implementation, the at least one mating member of the bottom portion includes at least one hollow male member extending from a side of the bottom vascular housing. Each of the at least one hollow male member includes a slot exposing an interior surface of the at least one hollow male member and a bottom aperture formed within an upward-facing coupling edge positioned proximal to a top surface of the bottom vascular housing. In this implementation, the at least one male/female member of the top portion includes at least one female member disposed at a downward-facing coupling edge of the top vascular housing. The at least one female member includes a top aperture for receiving the at least one hollow male member of the bottom portion.

In some cases, top and bottom portions can include at least one second male member and at least one second female member positioned on a side that opposes the other male and female members. In some cases, one of the at least one hollow male member or the at least one female member can include a hook that allows for insertion of the male member into the female member but prevents the removal of the male member from the female member.

In some cases, a diameter of an interior surface of the top vascular housing increases from a center of the top vascular housing to an outer longitudinal edge of the top vascular housing and a diameter of an interior surface of the bottom vascular housing increases from a center of the bottom vascular housing to an outer longitudinal edge of the bottom vascular housing.

A method of using a vascular access device with vessel accommodation according to certain implementations can include securing the top portion and the bottom portion together with a suture thread by inserting the suture thread through the bottom aperture of the at least one female member and the top aperture of the at least one hollow male member. The method further includes fastening the suture thread around the upward-facing coupling edge of the at least one female member and the downward-facing coupling edge of the at least one hollow male member. In some cases, fastening the suture thread around the upward-facing coupling edge of the at least one female member and the downward-facing coupling edge of the at least one hollow male member includes pulling excess suture thread, via the slot, from the interior surface of the at least one hollow male member until the suture thread is taut to the upward-facing coupling edge of the at least one female member and the downward-facing coupling edge of the at least one hollow male member and tying a surgical knot with two ends of the suture thread. In some cases, the suture thread is biodegradable. In some cases, sometime after the suture thread is fastened, an angioplasty can be performed on the vessel causing the top portion and/or bottom portion to move with respect to one another in a vertical direction.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Vascular access devices are described. A vascular access device with vessel accommodation can facilitate recovery and prevention of collapsed and damaged vessels. Advantageously, the described vascular access devices with vessel accommodation can help prevent damage to a vessel (including those supported by an AVF) as well as recover that vessel if/when that vessel is damaged and/or collapsed, therefore preventing or at least minimizing the likelihood of invasive and redundant surgeries. Furthermore, the described vascular access devices can also be placed around already collapsed portions of the vessel, making angioplasty easier and/or making recovery of a vessel that would otherwise be too damaged for an angioplasty recoverable.

A vascular access device with vessel accommodation is configured such that movement in linear horizontal and longitudinal directions, rotation around the horizontal and longitudinal axes, and rotation around the vertical axis may all be inhibited while top and bottom portions of the vascular access device are to move with respect to each other (e.g., separate and return) in a linear vertical direction (e.g., when an interventional radiologist performs an angioplasty on the portion of the vessel that is encased by the vascular access device). In some cases, additional features are provided that also minimize the likelihood of having a damaged and/or collapsed vessel in the first place, including damage that may otherwise be caused by the vascular access device itself.

As described herein, at least one "male/female member" refers to at least one first male member or at least one first female member (e.g., one or the other) and at least one "mating member" corresponding to the at least one male/female member refers to the other type of male/female that mates with the at least one first male member or the at least one first female member. For example, if the at least one "male/female member" is at least one male member, then the at least one "mating member" is at least one female member. As another example, if the at least one "male/female member" is at least one female member, then the at least one "mating member" is at least one male member.

Figures 1A, 1B, 1C:
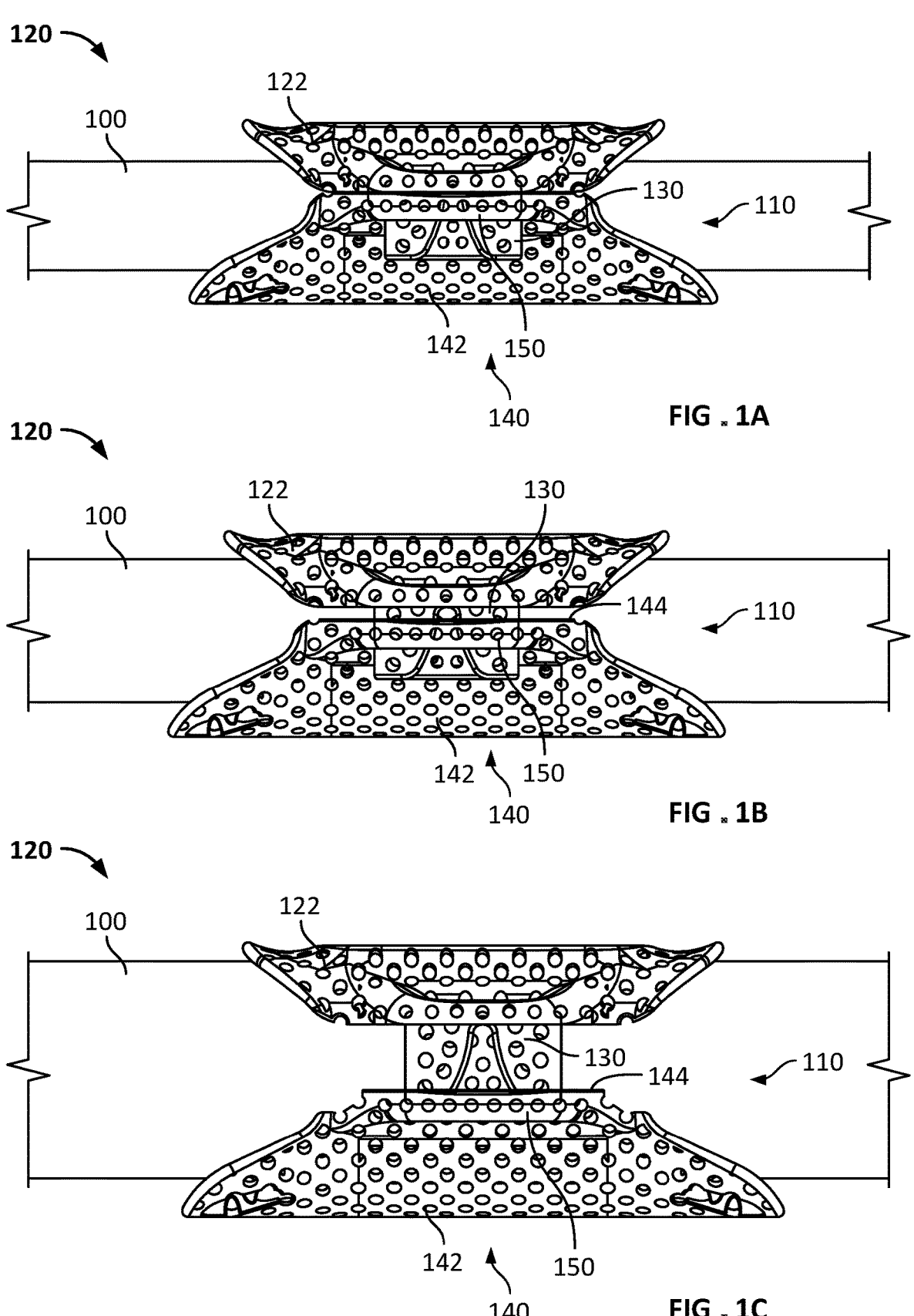
FIGS. 1A-1C illustrate linear vertical movement of top and bottom portions of a vascular access device with vessel accommodation.

FIGS. 1A-1C illustrate linear vertical movement of top and bottom portions of a vascular access device with vessel accommodation. Referring to FIGS. 1A-1C, a segment of a vessel 100 is encased by a vascular access device 110 with vessel accommodation. The vascular access device 110 includes a top portion 120 and a bottom portion 140. The top portion 120 includes a top vascular housing 122 that is used to encase a top portion of the vessel 100 when implanted and a male/female member in the form of at least one hollow male member 130 extending from the top vascular housing 122. The bottom portion 140 includes a bottom vascular housing 142 that is used to encase a bottom portion of the vessel 100 when implanted and a mating member in the form of at least one female member 150 disposed at an upward-facing coupling edge 144 of the bottom vascular housing 142. The top portion 120 and the bottom portion 140 are not monolithic with one another.

As can be seen, the at least one female member 150 of the bottom portion 140 receives the at least one hollow male member 130 of the top portion 120. Furthermore, as the size of the vessel 100 increases (e.g., FIG. 1A illustrates an initial/smaller size of the vessel 100, FIG. 1B illustrates an increased/larger size of the vessel 100, and FIG. 1C illustrates a final/maximum size of the vessel 100), the at least one hollow male member 130 of the top portion 120 can move vertically within the at least one female member 150 of the bottom portion 140 to accommodate the increased size of the vessel 100. The coupling between the at least one hollow male member 130 of the top portion 120 and the at least one female member 150 of the bottom portion 140 allows for controlled movement of the top and bottom portions 120, 140 to accommodate the vessel 100 becoming enlarged. For instance, the vessel 100 may already be at an increased size; in other scenarios, the size of the vessel 100 may increase over time in response to the creation of an AVF, an angioplasty performed by an interventional radiologist, or some other reason. Advantageously, the vascular access device 110 accommodates varying sizes of a vessel 100 (e.g., over time as the vessel enlarges) by way of the at least one hollow male member 130 and the at least one female member 150.

Although the top vascular housing 122 of the top portion 120 and the bottom vascular housing 142 of the bottom portion 140 may not be touching one another and/or covering the entire circumference of that cross-section of the vessel 100, the top vascular housing 122 and the bottom vascular housing 142 still, when combined around that portion of the vessel 100, prevent an "unsuccessful cannulation" or a "bad puncture," which refers to when a needle/cannula damages more tissue than necessary to be placed in the vein, whether the needle/cannula is actually placed in the vein (or not). Examples of a bad puncture include when a needle/cannula goes into the vein and out of a wall of the vessel 100, or when the vessel 100 is missed altogether, both of which can damage the vein and/or the tissue surrounding the vein and can contribute to the collapse of the vein or even the AVF (if applicable). Such a bad puncture can cause blood loss into the surrounding tissue and formation of a hematoma, and cause major discomfort to the patient.

Figure 2A:
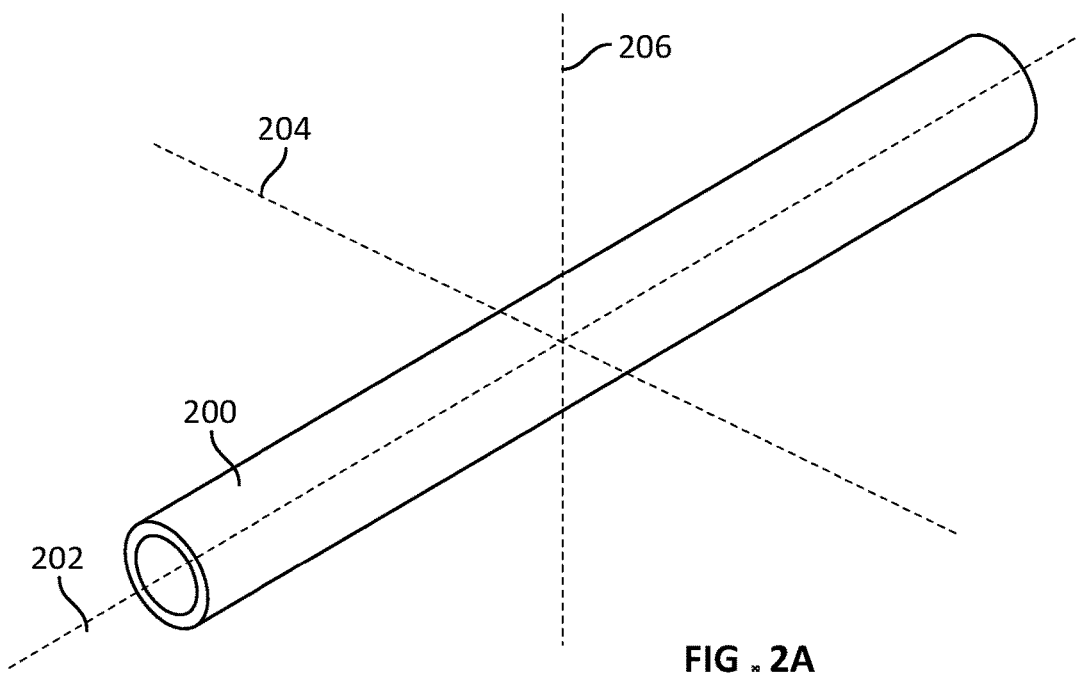
FIGS. 2A-2D illustrate insertion of a top portion and bottom portion of a vascular access device around a vessel.

FIGS. 2A-2D illustrate insertion of a top portion and bottom portion of a vascular access device around a vessel. FIG. 2A illustrates a vessel 200 with respect to three dimensional axes. In particular, a longitudinal axis 202 is orientated along a length of the vessel 200, a horizontal axis 204 is orientated perpendicular to the length of the vessel 200 in a horizontal plane, and a vertical axis 206 is orientated perpendicular to the length of the vessel 200 in a vertical plane. It should be understood that the vertical and horizontal planes are described in regard to the position of a surface of a patient's skin; a patient's movement (e.g., laying down or standing up) does not change the orientation of the longitudinal axis 202, the horizontal axis 204, and/or the vertical axis 206 because these axes 202, 204, 206 are described in relation of the vessel 200 to the surface of the patient's skin.

Figure 2B:
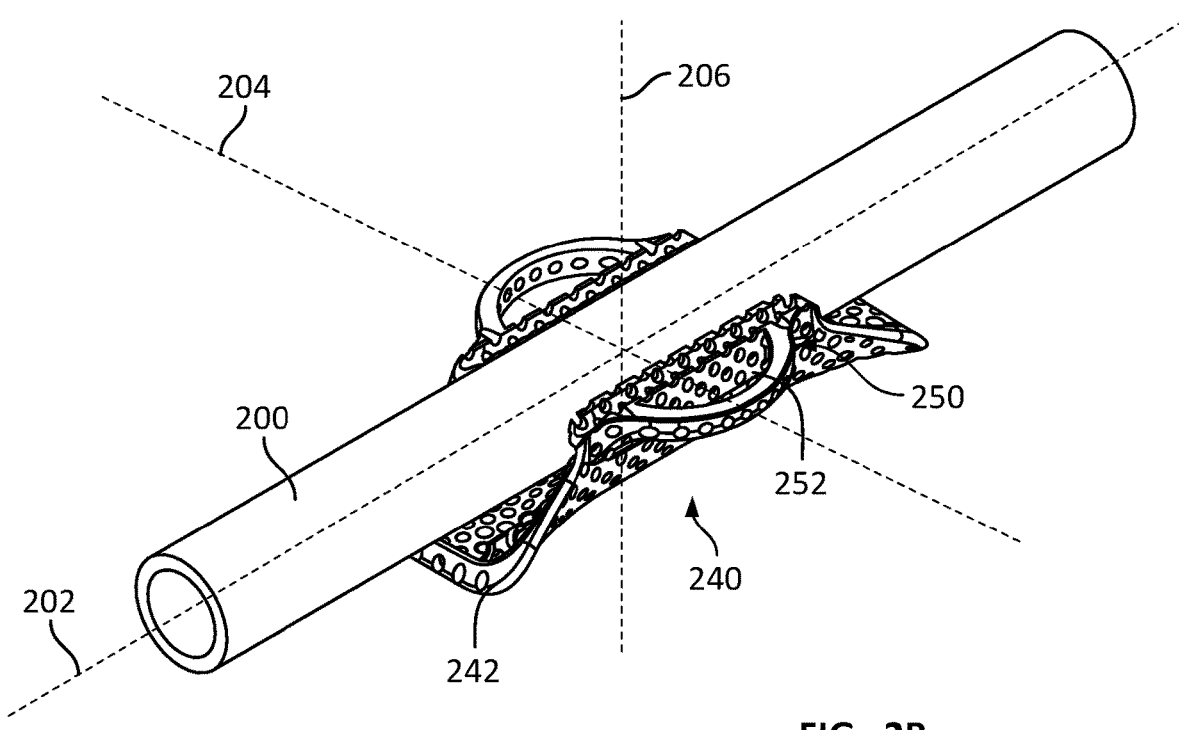

FIG. 2B illustrates a bottom portion 240 of a vascular access device 210 with vessel accommodation. When implanting the vascular access device 210, a surgeon can position the bottom vascular housing 242 of the bottom portion 240 underneath and then around a bottom portion of the vessel 200. This leaves the female member 250 of the bottom portion 240 with an aperture 252 positioned to receive a hollow male member of a top portion (not shown in this Figure).

Figures 2C, 2D:
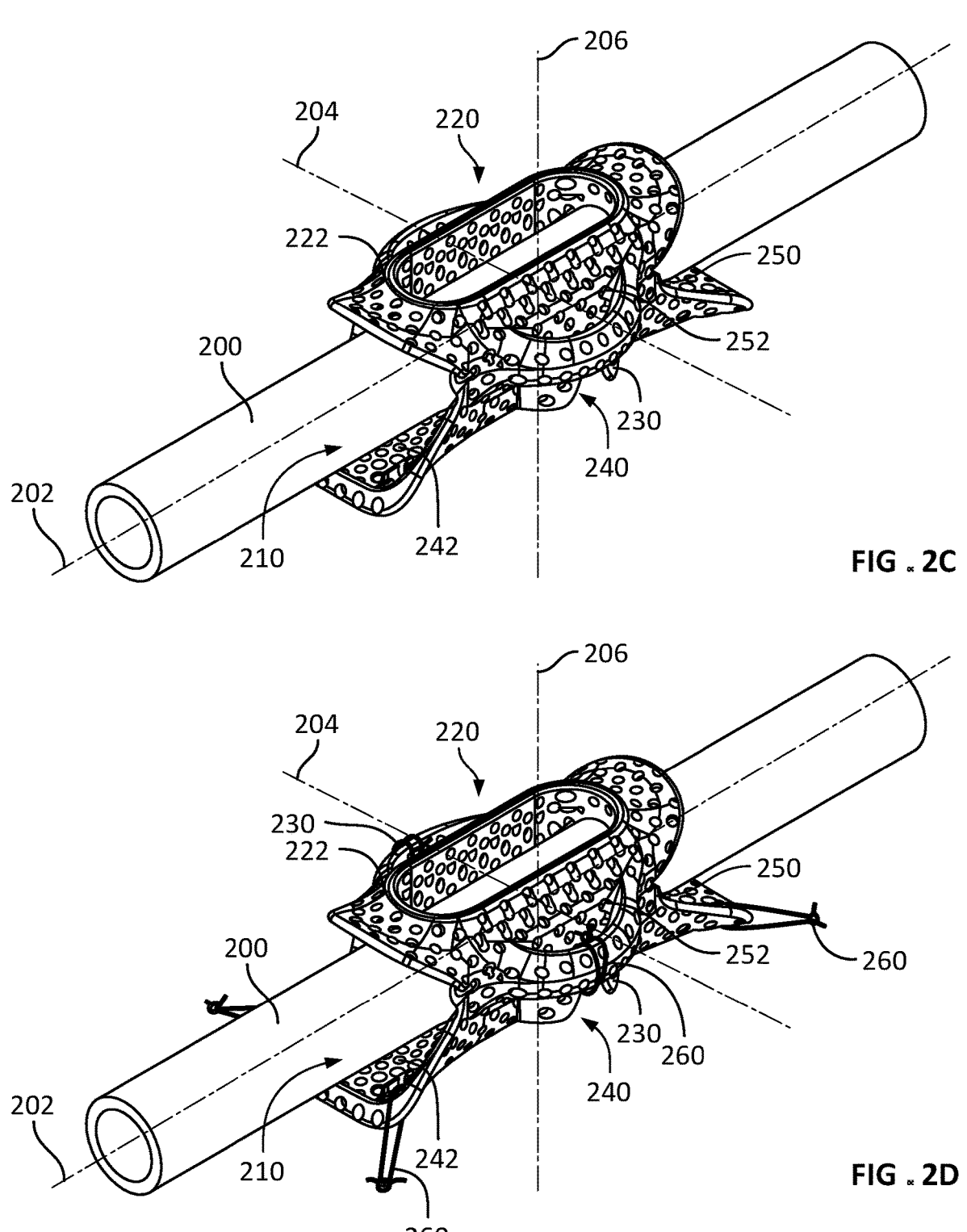
Figures 3A, 3B, 3C, 3D:
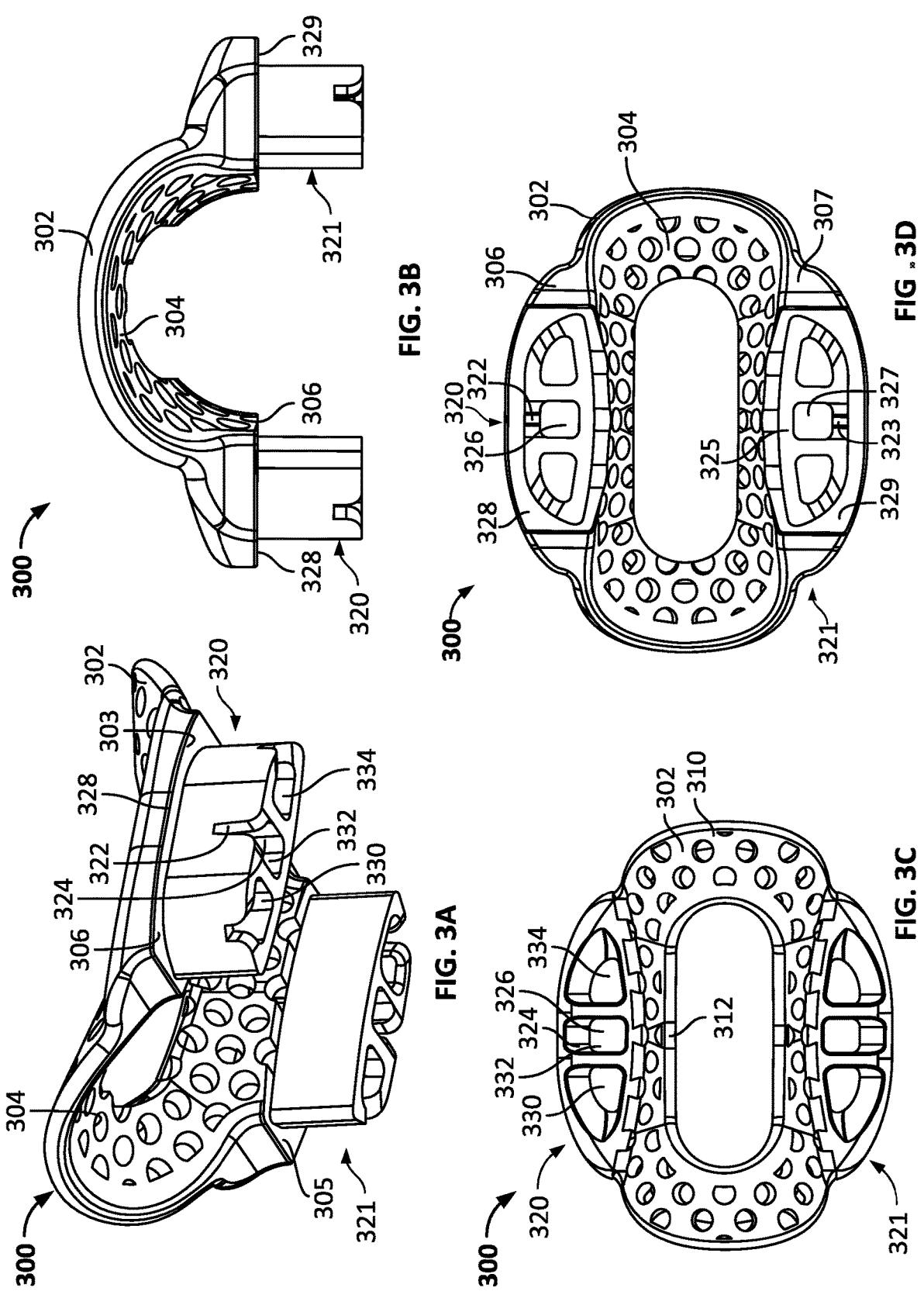
FIGS. 3A-3D illustrate various views of a top portion of a vascular access device.
Figure 4A:
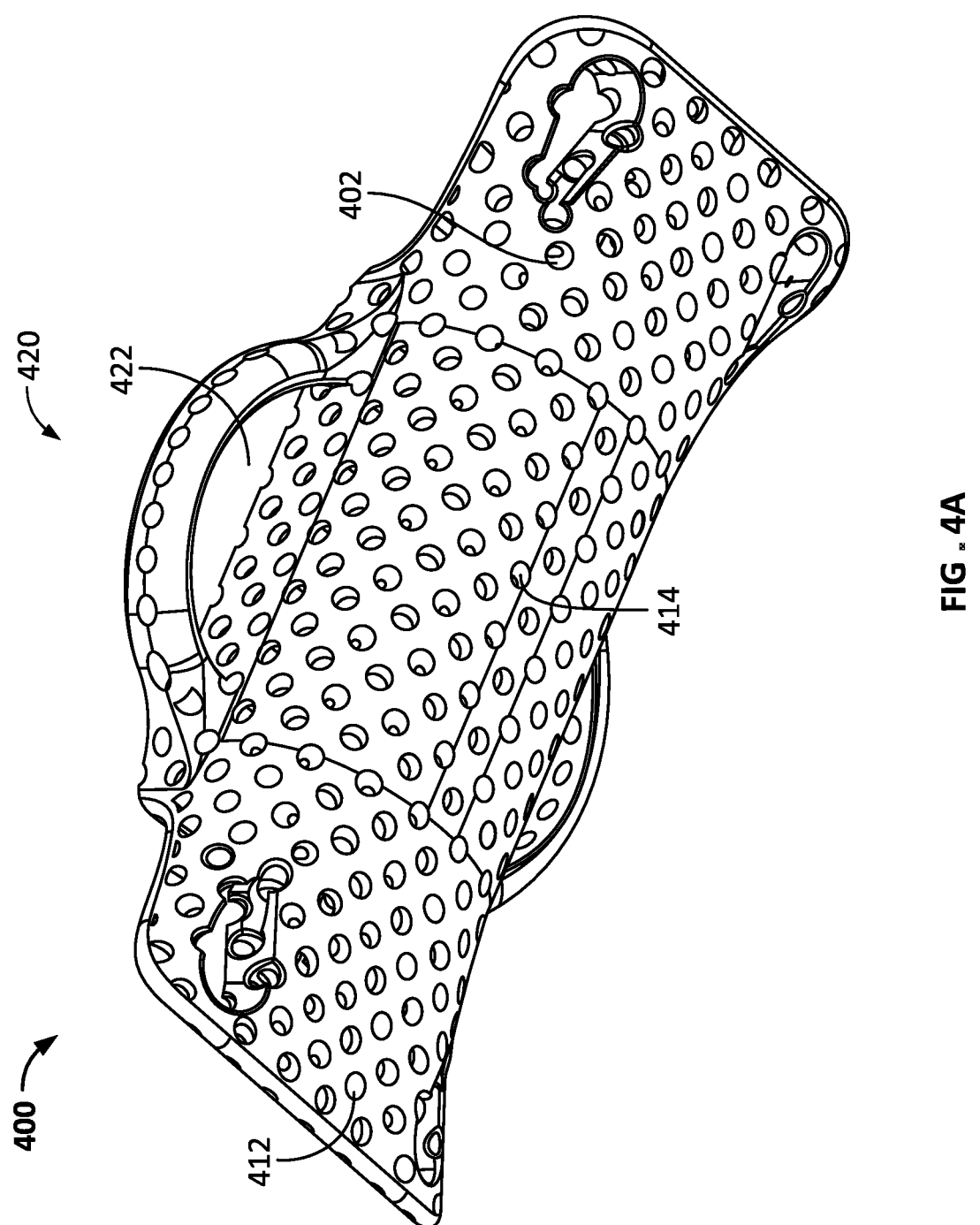
FIGS. 4A-4D illustrate various views of a bottom portion of a vascular access device.
Figure 4B:
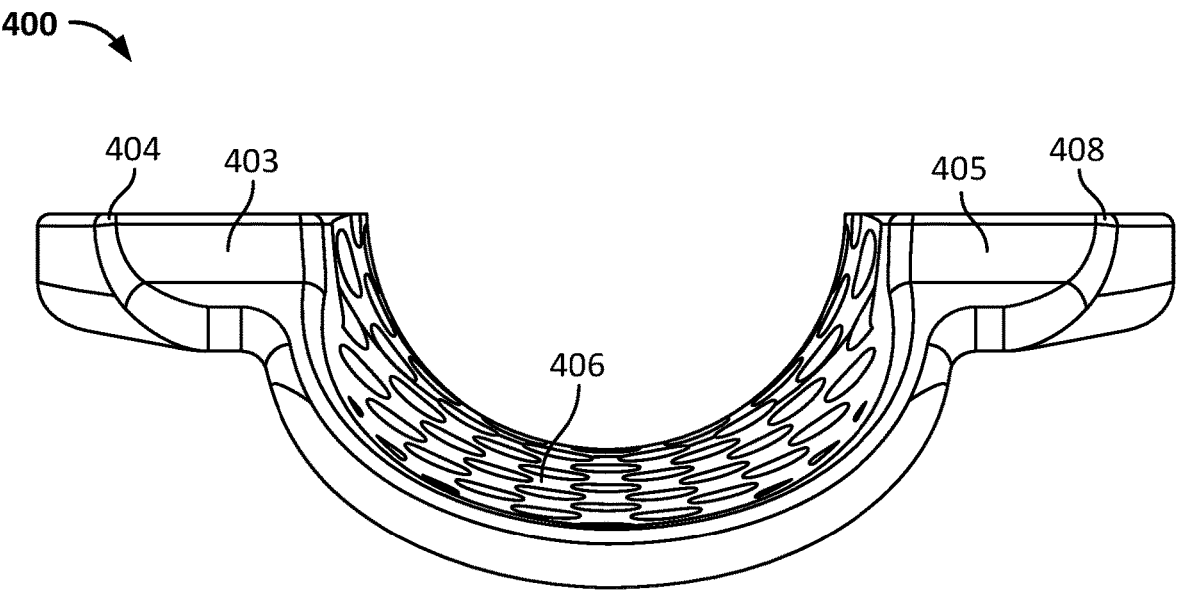
Figure 4C:
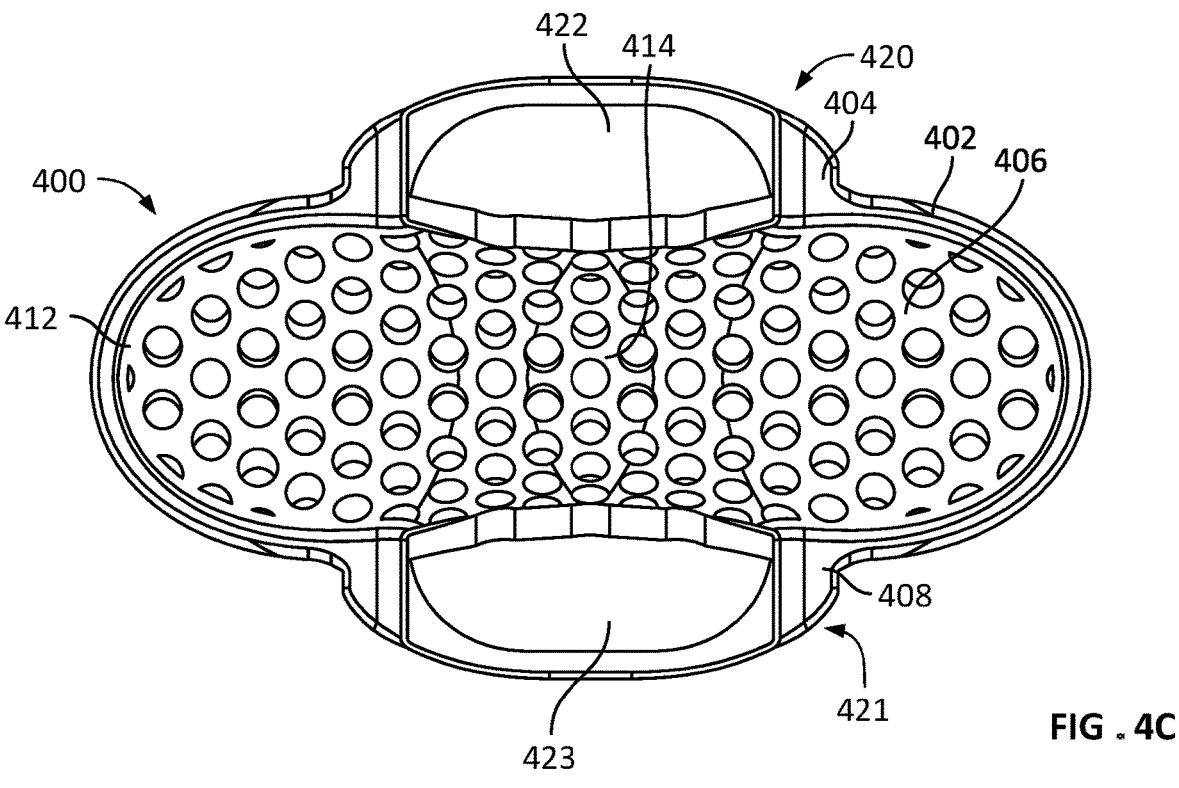
Figure 4D:
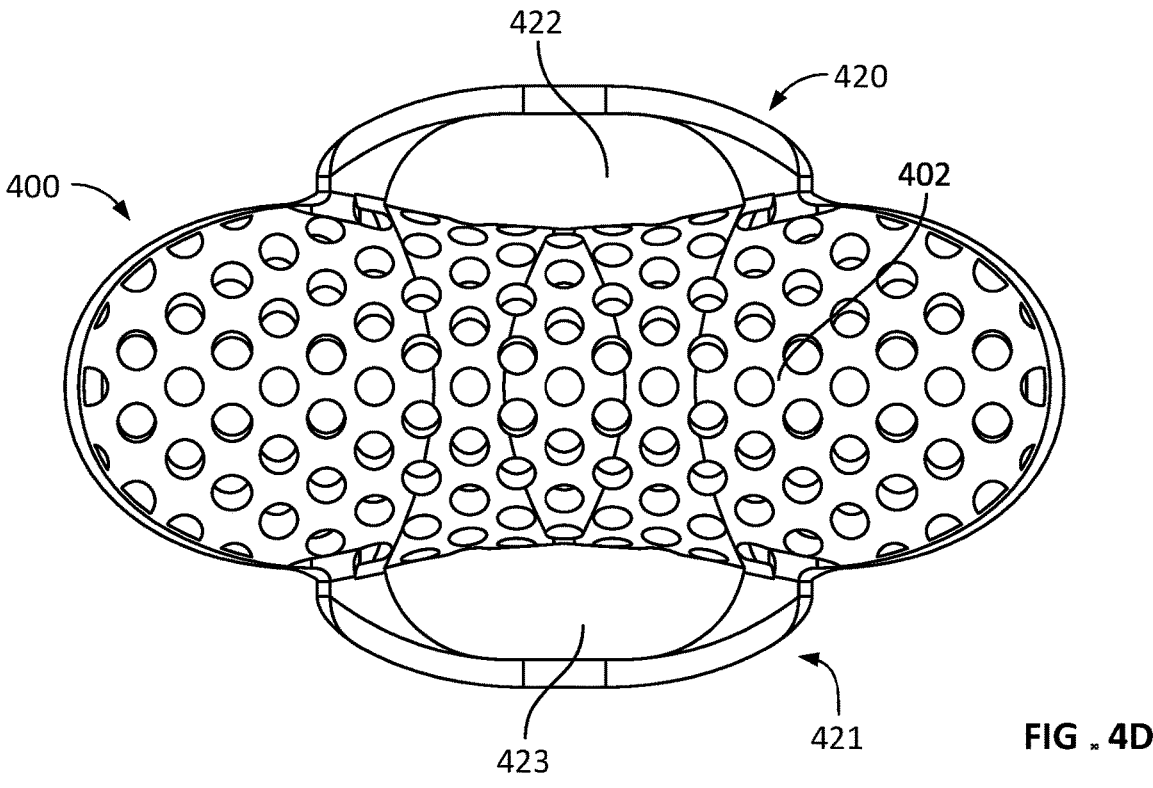

FIG. 2C illustrates a top portion 220 and a bottom portion 240 of a vascular access device 210 with vessel accommodation. When implanting the vascular access device 210, a surgeon can position the top vascular housing 222 of the top portion 220 over and around a top portion of the vessel 200 by inserting the hollow male member 230 of the top portion 220 into the aperture 252 of the female member 250 of the bottom portion 240. FIG. 2D illustrates a vascular access device 210 having sutures 260 securing the top portion 220 to the bottom portion 240 around the vessel 200 via the hollow male member 230 of the top portion 220 and the female member 250 of the bottom portion 240, as is explained in more detail below with respect to FIG. 6. The sutures 260 can also be used to attach only to the bottom portion 240 and the surrounding tissue to prevent unwanted movement/rotation of the vascular access device 210.

FIGS. 3A-3D illustrate various views of a top portion of a vascular access device. Referring to FIGS. 3A-3D, a top portion 300 of a vascular access device includes a top vascular housing 302 and at least one hollow male member 320 extending from a side 303 of the top vascular housing 302. The top vascular housing 302 is shaped to form around a top portion of a vessel (i.e., encase the top portion of the vessel) when implanted. In some cases, an interior surface 304 of the top vascular housing 302 has a curvature to fit around the top portion of the vessel by matching a relative curvature (e.g., cylindrical) of the top portion of the vessel. In some cases, the interior surface 304 of the top vascular housing 302 may have relatively flat horizontal-facing and/ or vertical-facing sides with little to no curvature between the horizontal-facing and vertical-facing sides. In some cases, a longitudinal length of the top vascular housing 302 is greater at a position that is proximal to a surface of a patient's skin when implanted (e.g., $L_{proximal}$) than a longitudinal length of the top vascular housing 302 at a position that is distal to the surface of a patient's skin when implanted (e.g., $L_{distal}$). Advantageously, the extension in the longitudinal direction at a position that is proximal to the surface of the patient's skin (e.g., $L_{proximal}$) protects the vessel from bad punctures while also providing a smooth contour/profile that decreases the risk of damage to the vessel caused by the vascular access device itself.

Each of the at least one hollow male member 320 includes a slot 322 exposing an interior surface 324 of that hollow male member and a top aperture 326 formed within a downward-facing coupling edge 328. In some cases, the downward-facing coupling edge 328 is positioned proximal to a bottom surface 306 of the top vascular housing 302. In some cases, the downward-facing coupling edge 328 of the at least one hollow male member 320 is at an end of the slot 322 that, when implanted, is proximal to a surface of a patient's skin (e.g., highest vertical point of the at least one hollow male member 320).

In some cases, the top portion 300 also includes at least one second hollow male member 321 extending from an opposing side 305 of the top vascular housing 302 that is opposite of the side 303 of the top vascular housing 302 that the at least one hollow male member 320 extends from. In other words, the at least one second hollow male member 321 extends from a position of the top vascular housing 302 that is opposite of a position from which the at least one hollow male member 320 extends from the top vascular housing 302 (e.g., an opposing position). Each of the at least one second hollow male member 321 includes a slot 323 exposing an interior surface 325 of that hollow male member and a top aperture 327 formed within a downward-facing coupling edge 329. In some cases, the downward-facing coupling edge 329 is placed proximal to a second bottom surface 307 of the top vascular housing 302.

In some cases, a diameter of an interior surface 304 of the top vascular housing 302 is greater at an outer longitudinal edge 310 than at a center 312. In other words, the diameter of the interior surface 304 of the top vascular housing 302 increases from the center 312 of the top vascular housing 302 to the outer longitudinal edge 310 of the top vascular housing 302. In some cases, this variation in diameter between the outer longitudinal edge 310 and the center 312 allows for a vessel to become enlarged over time while still providing a smooth contour for the vessel. Advantageously, the increased diameter towards the outer longitudinal edge 310 allows for the vessel to avoid being pinched by the ends of the access device when/if the vessel expands beyond the diameter accommodated by the male/female members of the top and bottom portions.

The increased diameter can also protect the vessel from bad punctures while providing a smooth contour/profile that decreases the risk of damage to the vessel caused by the vascular access device itself. In some cases, there are no "sharp" edges anywhere on the top portion 300 that would damage and/or cut the skin, vessel, and/or tissue surrounding the top portion 300. Furthermore, the interior surface 304 of the top vascular housing 302 includes smooth, curved contours that do not interfere with the flow of the blood within the vessel.

In some cases, the at least one hollow male member 320 of the top portion 300 is three hollow male members 330, 332, 334. In some cases, the slot 322 of the middle hollow male member 332 is located in the middle of an outside surface of the middle hollow male member 332 (e.g., at a 90 degree angle from the longitudinal axis 202 in the horizontal plane). In some cases, the slot 322 for each of the two outside hollow male members 330, 334 is located at an angle/corner of the two outside hollow male members 330, 334 (e.g., at a 45 degree and/or 135 degree angle from the longitudinal axis 202 in the horizontal plane).

In some cases, all surfaces of the top portion 300 are porous. In some cases, through and through pores (e.g., holes) are included in the top portion 300 in all directions (e.g., horizontal, vertical, and longitudinal axes 202, 204, 206 of FIG. 2A) to enhance soft tissue integration. In some cases, all surfaces of the top portion 300 are roughened to enhance soft tissue integration. In some cases, the porousness, through and through holes, and/or roughened surfaces may be accomplished through the use of acid etching, 3D printing, or texturing in the manufacture of the top portion 300. It should be understood that the porousness, through and through holes, and/or roughened surfaces are sized to enhance tissue integration and do not create "sharp" edges that could cut and/or damage the vessel or surrounding tissue.

FIGS. 4A-4D illustrate various views of a bottom portion of a vascular access device. Referring to FIGS. 4A-4D, a bottom portion 400 of a vascular access device includes a bottom vascular housing 402 and at least one female member 420 disposed at an upward-facing coupling edge 404 on a side 403 of the bottom vascular housing 402. The bottom vascular housing 402 is shaped to form around a bottom portion of a vessel (i.e., encase the bottom portion of the vessel) when implanted. In some cases, an interior surface 406 of the bottom vascular housing 402 has a curvature to fit around the bottom portion of the vessel by matching a relative curvature (e.g., cylindrical) of the bottom portion of the vessel. In some cases, the interior surface 406 of the bottom vascular housing 402 may have relatively flat horizontal-facing and/or vertical-facing sides with little to no curvature between the horizontal-facing and vertical-facing sides. The at least one female member 420 includes a bottom aperture 422 for receiving the at least one hollow male member of the top portion (e.g., at least one hollow male member 320 of the top portion 300 as illustrated in FIGS. 3A-3D).

In some cases, a longitudinal length of the bottom vascular housing 402 is greater at a position that is distal to a surface of a patient's skin when implanted (e.g., $L_{distal}$) than a longitudinal length of the bottom vascular housing 402 at a position that is proximal to the surface of a patient's skin when implanted (e.g., $L_{proximal}$). Advantageously, this added longitudinal length of the bottom vascular housing 402 at a position that distal to a surface of a patient's skin when implanted (e.g., $L_{distal}$) can help prevent a bad puncture while also providing a smooth contour/profile that decreases the risk of damage to the vessel caused by the vascular access device itself.

In some cases, bottom portion 400 also includes at least one second female member 421 disposed at a second upward-facing coupling edge 408 on an opposing side 405 of the bottom vascular housing 402 that is opposite of the side 403 of the coupling edge in which the at least one female member 420 is disposed. In other words, the at least one second female member 421 is located at a position that is opposite of a position of the at least one female member 420 disposed at the upward-facing coupling edge 404 of the bottom vascular housing 402. The at least one second female member 421 includes a bottom aperture 423 for receiving at least one second hollow male member of the top portion (e.g., at least one second hollow male member 321 of the top portion 300 as illustrated in FIGS. 3A-3D).

Referring to FIGS. 3A-3D and FIGS. 4A-4D, in some cases, instead of or in addition to at least one second hollow male member 321 and at least one second female member 421, the top and bottom portions 300, 400 may be attached/coupled on one side via a hinge or some other similar attachment mechanism. In some these cases, the at least one hollow male member 320 and at least one female member 420 of the top and bottom portions 300, 400 provide the ability to move vertically with respect to one another.

Referring back to FIGS. 4A-4D, in some cases, a diameter of the interior surface 406 of the bottom vascular housing 402 is greater at an outer longitudinal edge 412 than at a center 414. In other words, the diameter of the interior surface 406 of the bottom vascular housing 402 increases from the center 414 of the bottom vascular housing 402 to the outer longitudinal edge 412 of the bottom vascular housing 402. In some cases, this variation in diameter between the outer longitudinal edge 412 and the center 414 allows for a vessel to become enlarged over time while still providing a smooth contour for the vessel. Advantageously, the increased diameter towards the outer longitudinal edge 412 allows for the vessel to avoid being pinched by the ends of the access device when/if the vessel expands beyond the diameter accommodated by the male/female members of the top and bottom portions.

The increased diameter can also protect the vessel from bad punctures while providing a smooth contour/profile that decreases the risk of damage to the vessel caused by the vessel itself. In some cases, there are no "sharp" edges anywhere on the bottom portion 400 that would damage and/or cut the skin, vessel, and/or tissue surrounding the bottom portion 400. Furthermore, the interior surface 406 of the bottom vascular housing 402 includes smooth, curved contours that do not interfere with the flow of the blood within the vessel.

In some cases, all surfaces of the bottom portion 400 are porous. In some cases, through and through pores (e.g., holes) are included in the bottom portion 400 in all directions (e.g., horizontal, vertical, and longitudinal axes 202, 204, 206 of FIG. 2A) to enhance soft tissue integration. In some cases, all surfaces of the bottom portion 400 are roughened to enhance soft tissue integration. In some cases, the porousness, through and through holes, and/or roughened surfaces may be accomplished through the use of acid etching, 3D printing, or texturing in the manufacture of the bottom portion 400. It should be understood that the porousness, through and through holes, and/or roughened surfaces are sized to enhance tissue integration and do not create "sharp" edges.

Referring to FIGS. 3A-3D and FIGS. 4A-4D, in some cases, the at least one hollow male member 320 includes a hook or hook-type configuration. The hook or hook-type configuration prevents decoupling of the at least one hollow male member 320 of the top portion 300 from the at least one female member 420 of the bottom portion 400 upon receipt of the of the at least one hollow male member 320 by the at least one female member 420. It should be understood that the hook or hook-type configuration would prevent decoupling of the at least one hollow male member 320 of the top portion 300 from the at least one female member 420 of the bottom portion 400 in the case of an interventional radiologist performing an angioplasty on the vessel, but would not prevent decoupling of the at least one hollow male member 320 of the top portion 300 from the at least one female member 420 of the bottom portion 400 in the case of surgery to remove the vascular access device.

It should be understood that while there can be any reasonable number of hollow male members 320; there just needs to be at least one hollow male member. In some cases, the shape of the at least one hollow male member 320 substantially matches that of the bottom aperture 422 of the at least one female member 420 to prevent all movement (e.g., rotational and/or linear) of the top and bottom portions 300, 400 in horizontal and/or longitudinal directions/axes and prevent rotational movement around the vertical axis when the top portion 300 and/or the bottom portion 400 are affixed to tissue surrounding the vessel. In other words, when the top portion 300 and the bottom portion 400 are coupled to one another around a vessel and affixed to tissue surrounding the vessel, a fit of the at least one hollow male member 320 of the top portion 300 within the at least one female member 420 of the bottom portion 400 prevents all movement of the top portion 300 and/or the bottom portion 400 with respect to one another in horizontal and/or longitudinal directions while allowing movement of the top portion 300 and/or the bottom portion 400 with respect to one another in a linear vertical direction. It should be understood that the top portion 300 and/or the bottom portion 400 can be affixed to tissue surrounding the vessel in a number of ways, including but not limited to via suture thread, tissue in-growth around the top portion 300 and/or the bottom portion 400 (e.g., that is promoted over time via surface features of the top portion 300 and/or the bottom portion 400), and other ways of affixing implanted devices to tissue known to those skilled in the art.

Referring to FIGS. 3C, 3D, 4C, and 4D, although a shape of the at least one hollow male member 320 and the at least one female member 420 is illustrated as being substantially rectangular in shape in the horizontal plane, in some cases, the shape of the at least one hollow male member 320 and the at least one female member 420 can be square, triangular, circular, pentagonal, hexagonal, heptagonal, octagonal, ovoidal, or irregular/puzzle piece shaped in shape in the horizontal plane. In some cases, the shape of the at least one hollow male member 320 and the at least one female member 420 can also include corresponding indentations and other features that can be used to prevent movement of the top portion 300 and/or the bottom portion 400 in horizontal and/or longitudinal directions/axes and prevent rotational movement around the vertical axis.

Figures 5A, 5B, 5C, 5D:
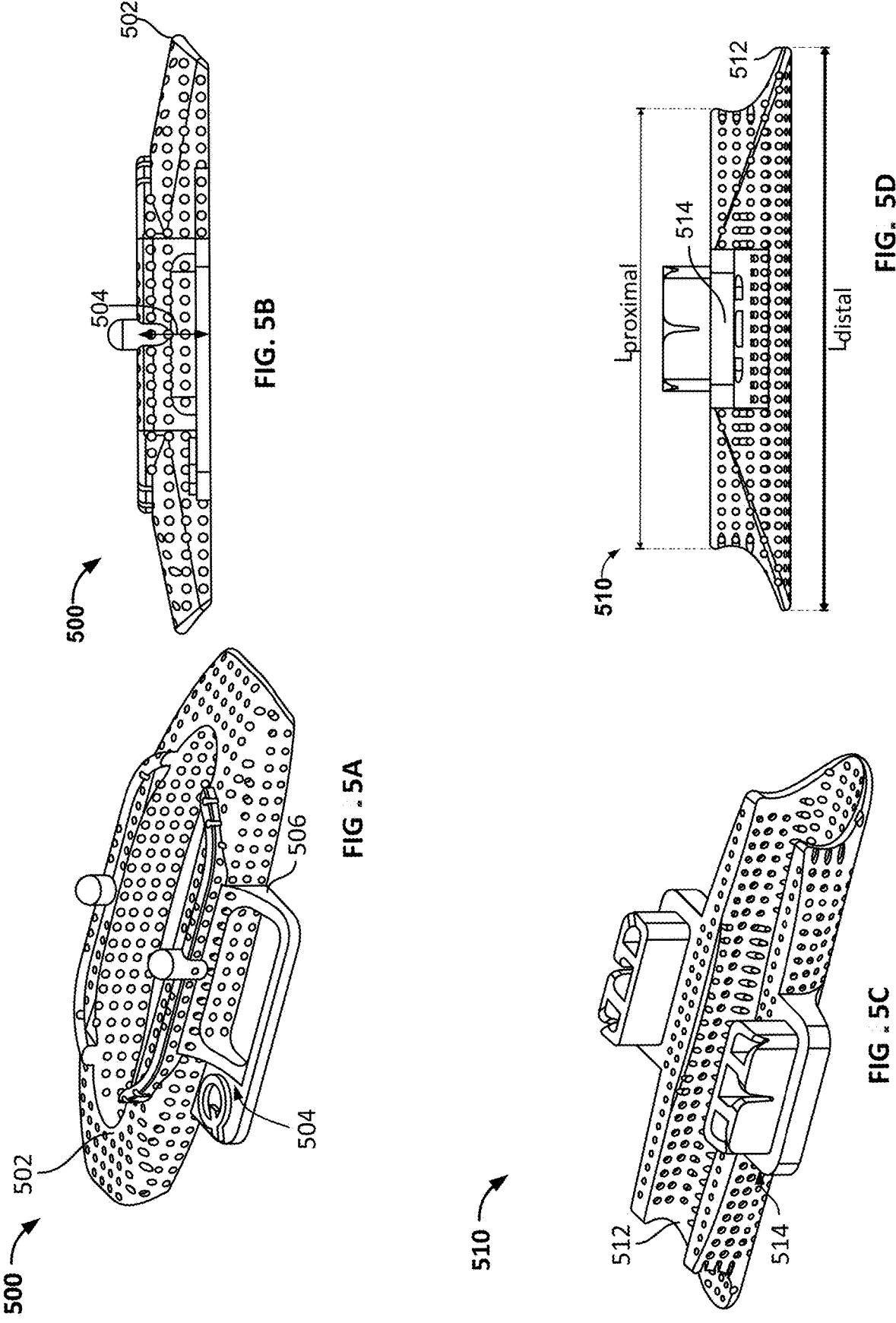
FIGS. 5A-5D illustrate views of a top portion having a female member and a bottom portion having a male member.

FIGS. 5A-D illustrate views of a top portion having a female member and a bottom portion having a male member. Referring to FIGS. 5A and 5B, a top portion 500 of a vascular access device includes a top vascular housing 502 and a male/female member in the form of at least one female member 504 disposed at a downward-facing coupling edge

506 of the top vascular housing 502. It should be understood that the top portion 500 may have any of the features described above with respect to the at least one female member 420 of FIGS. 4A-4D. Referring to FIGS. 5C and 5D, a bottom portion 510 of a vascular access device includes a bottom vascular housing 512 and a mating member in the form of at least one hollow male member 514 extending from the bottom vascular housing 512. It should be understood that the bottom portion 510 may have any of the features described above with respect to the at least one hollow male member 320 of FIGS. 3A-3D. Furthermore, in some cases, the top portion may have a male member on one side of the top vascular housing and a female member on an opposite side of the top vascular housing; and the bottom portion may have a female member on one side of the bottom vascular housing that corresponds to the male member of the top portion and a male member on an opposite side of the bottom vascular housing that corresponds to the female member of the top portion.

Figure 6:
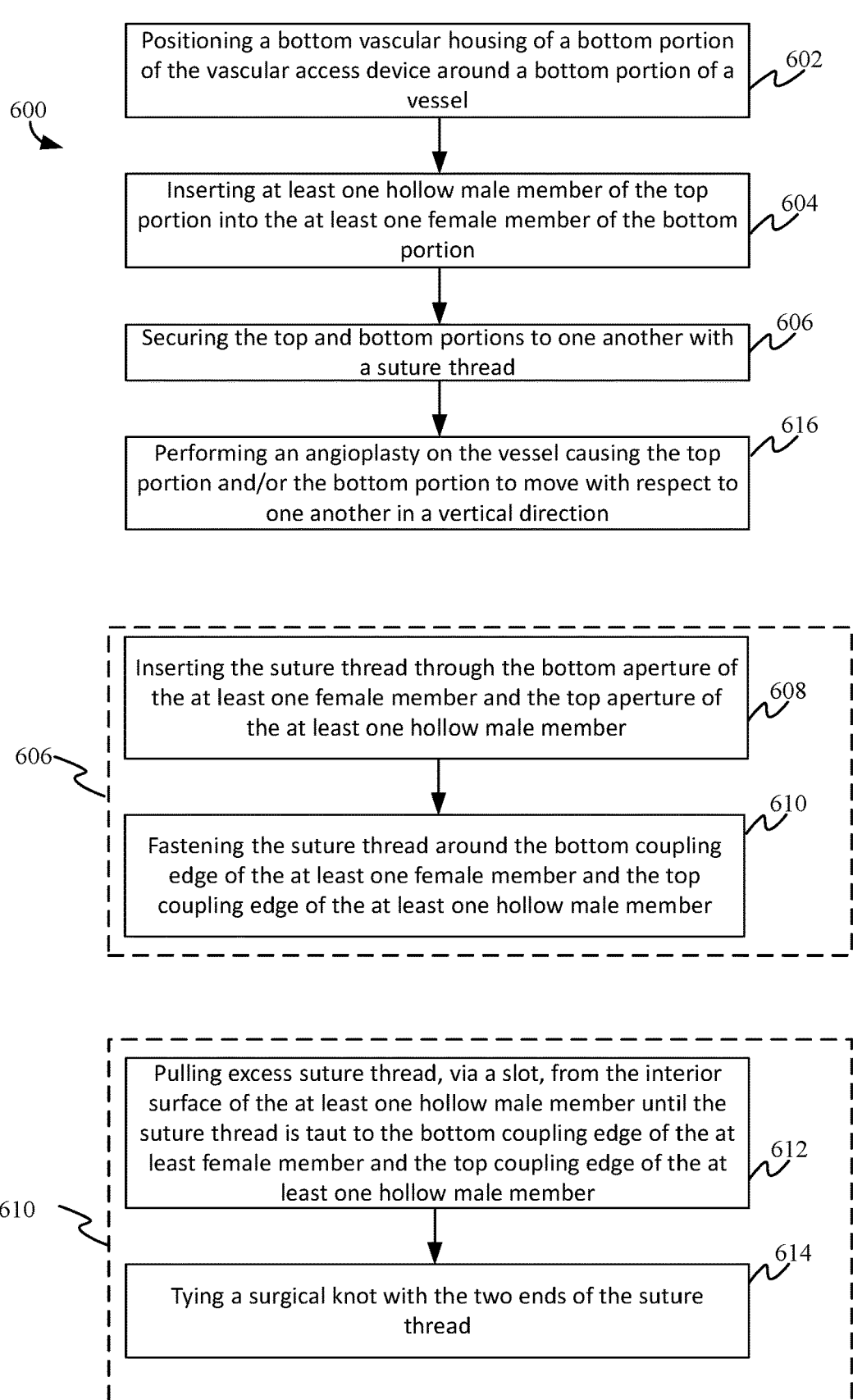
FIG. 6 illustrates a method of implanting a vascular access device and subsequent angioplasty.

FIG. 6 illustrates a method of implanting a vascular access device and subsequent angioplasty. A method 600 of implanting a vascular access device includes positioning (602) a bottom vascular housing of a bottom portion of the vascular access device around a bottom portion of a vessel. This simultaneously positions a bottom aperture of at least one female portion of the bottom portion of the vascular access device to vertically receive at least one hollow male member of a top portion of the vascular access device. The method 600 continues by inserting (604) the at least one hollow male member of the top portion into the at least one female member of the bottom portion. This simultaneously positions the top vascular housing around a top portion of the vessel.

The method 600 continues by securing (606) the top and bottom portions to one another with a suture thread. In some cases, securing (606) the top and bottom portions to another with a suture thread includes inserting (608) the suture thread through the bottom aperture of the at least one female member and the top aperture of the at least one hollow male member and fastening (610) the suture thread around the upward-facing coupling edge of the bottom vascular housing and the downward-facing coupling edge of the at least one hollow male member.

In some cases, fastening (610) the suture thread around the upward-facing coupling edge of the bottom vascular housing and the downward-facing coupling edge of the at least one hollow male member includes pulling (612) excess suture thread, via the slot of the at least one hollow male member, from the interior surface of the at least one hollow male member until the suture thread is taut to the upward-facing coupling edge of the bottom vascular housing and the downward-facing coupling edge of the at least one hollow male member and tying (614) a surgical knot with two ends of the suture thread. In some cases, the suture thread is biodegradable.

In some cases, the method 600 can continue by performing (616) an angioplasty on the vessel. As understood by interventional radiologists/surgeons, performing (616) an angioplasty on the vessel involves inserting a catheter through the vessel to the portion of the vessel that needs to be expanded (e.g., due to restriction of blood flow at that portion of the vessel caused by a blockage). A balloon with a stent around it is inflated to the appropriate size and then deflated and removed, leaving the stent at the appropriate size to allow adequate blood flow at that portion of the vessel. When the angioplasty is performed at a portion of the vessel encased by the vascular access device sometime after the suture thread is fastened (610), the expansion of the balloon causes the top portion and/or the bottom portion to move with respect to one another in a vertical direction. For instance, the top portion may move vertically towards the surface of the skin while the bottom portion may move vertically away from the surface of the skin. Therefore, a variable cross-sectional area of the complete housing (e.g., the combination of the top vascular housing of the top portion and the bottom vascular housing of the bottom portion) is formed when the at least one male/female member (e.g., the at least one male member of the top portion in this case) and the at least one mating member (e.g., the at least one female member of the bottom portion in this case) are coupled together to accommodate enlarging vessels. This movement, which only includes linear vertical movement, is accomplished by the at least one hollow male member of the top portion vertically sliding through the at least one female member of the bottom portion. As explained above, because of the configuration of the at least one hollow male member of the top portion and the at least one female member of the bottom portion, movement/rotation in horizontal and longitudinal directions/axes is prevented and rotation around the vertical axis is also prevented. This linear vertical movement is advantageous because it can extend the useful life of the vessel for medical treatment.

Figures 7A, 7B, 7C:
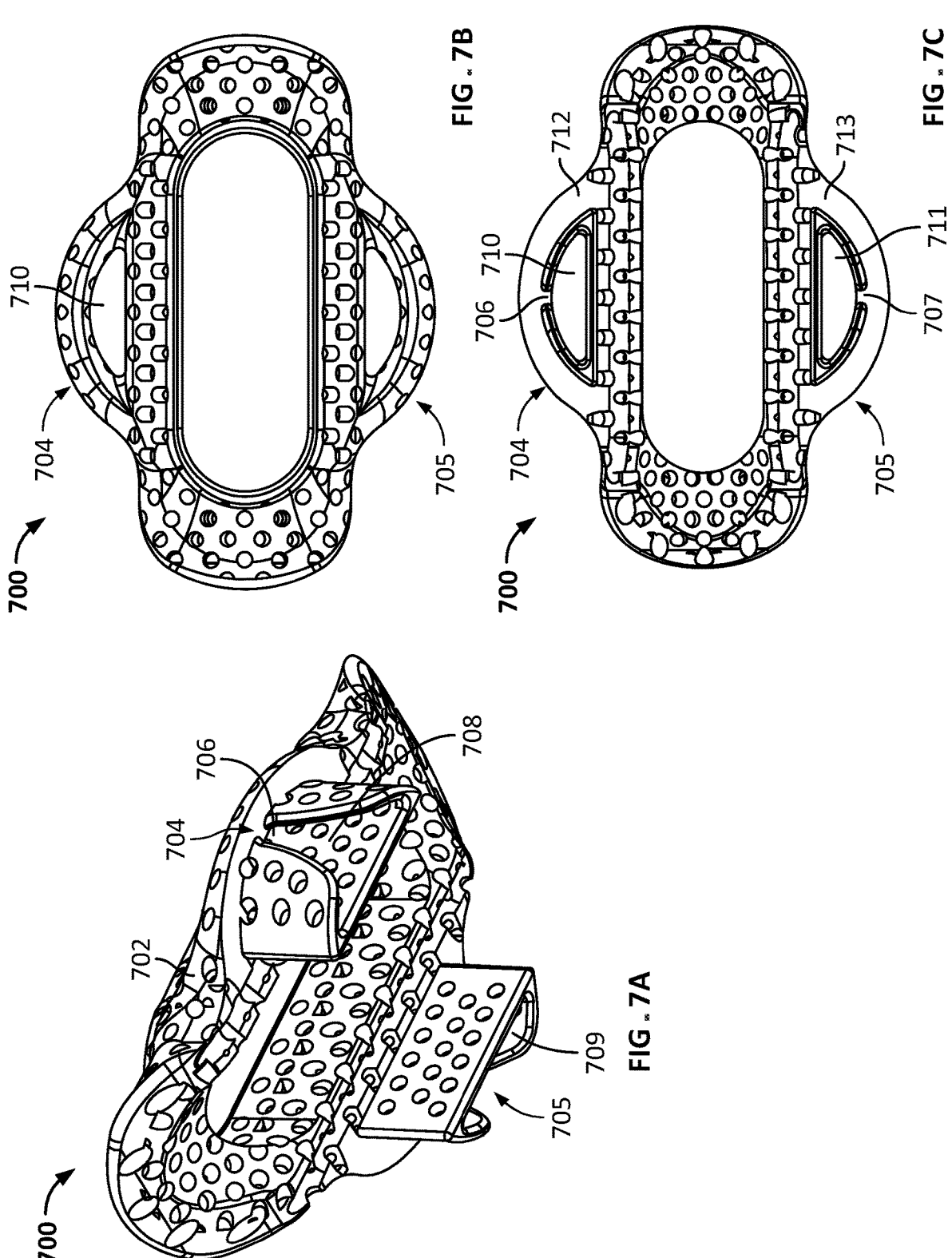
FIGS. 7A-7C illustrate various views of a top portion of a vascular access device.

FIGS. 7A-7C illustrate various views of a top portion of a vascular access device. The top portion 700 is similar to the top portion 300 described with respect to FIGS. 3A-3D, except the shape of the at least one hollow male member, as described below. Referring to FIGS. 7A-7C, a top portion 700 of a vascular access device includes a top vascular housing 702 and at least one hollow male member 704 extending from the top vascular housing 702. Each of the at least one hollow male member 704 includes a slot 706 exposing an interior surface 708 of that hollow male member 704 and a top aperture 710 formed within a downward-facing coupling edge 712.

In some cases, the top portion 700 includes at least one second hollow male member 705 extending from the top vascular housing 702. Each of the at least one second hollow male member 705 includes a slot 707 exposing an interior surface 709 of that hollow male member and a top aperture 711 formed within a downward-facing coupling edge 713.

Figure 8A:
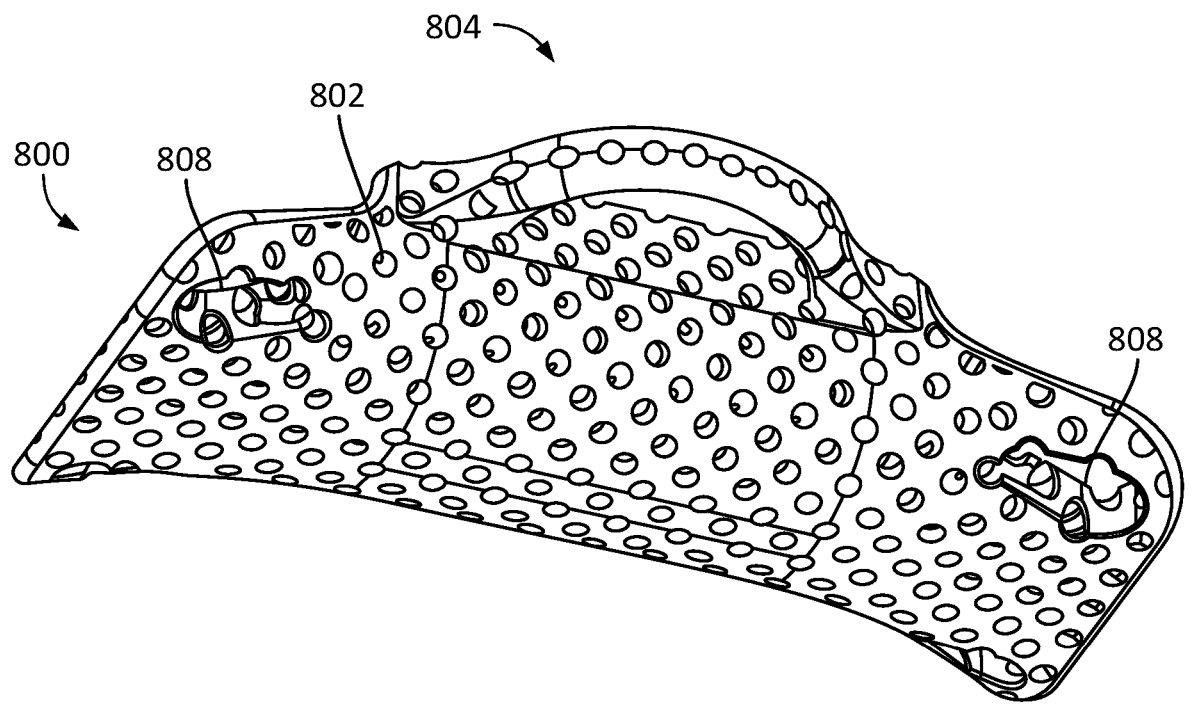
FIGS. 8A-8C illustrate various views of a bottom portion of a vascular access device.
Figure 8B:
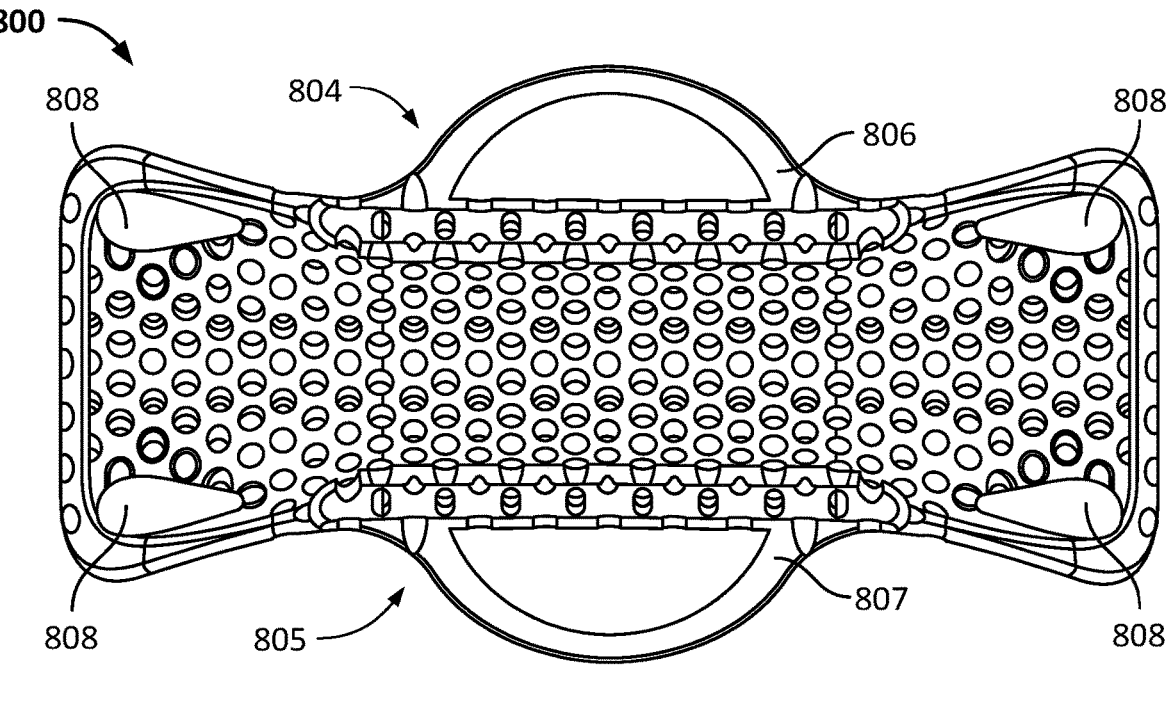
Figure 8C:
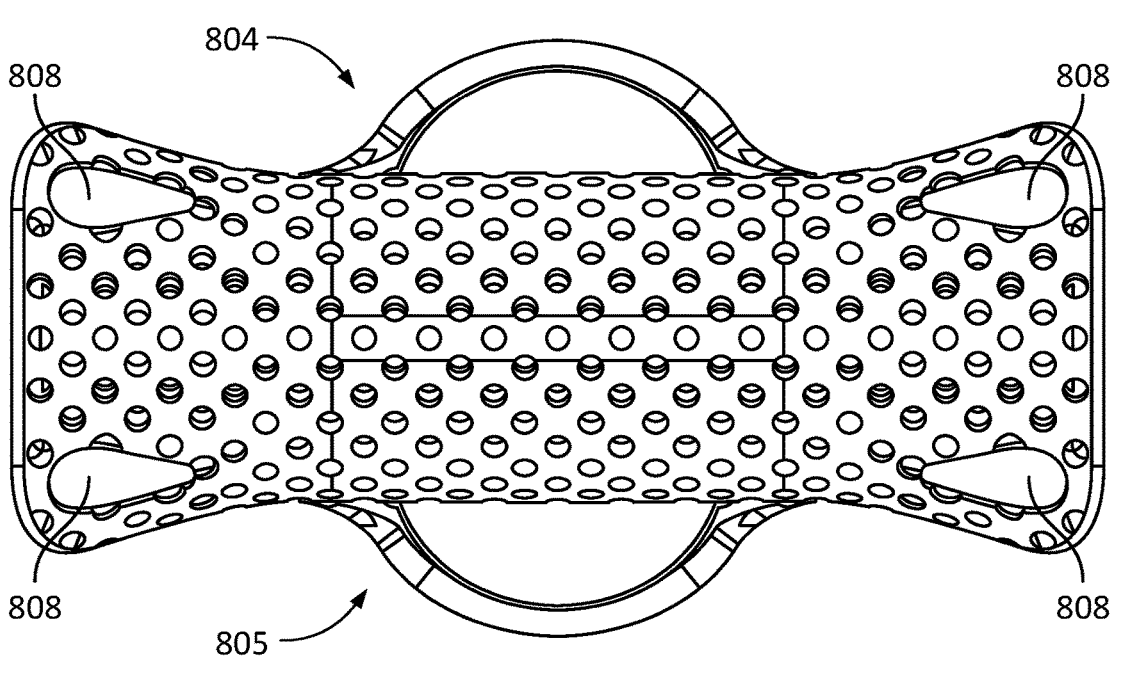

FIGS. 8A-8C illustrate various views of a bottom portion of a vascular access device. The bottom portion 800 is similar to the bottom portion 400 described with respect to FIGS. 4A-4D, except the shape of the at least one female member and the optional addition of at least one corner aperture, as described below. Referring to FIGS. 8A-8C, a bottom portion 800 of a vascular access device includes a bottom vascular housing 802 and at least one female member 804 disposed at an upward-facing coupling edge 806. The at least one female member 804 is configured to receive at least one hollow male member such as the at least one hollow male member 704 of FIGS. 7A-7C. In some cases, the bottom portion 800 further includes at least one second female member 805 disposed at a second upward-facing coupling edge 807. In some cases, the bottom portion further includes at least one corner aperture 808 that can be used to attach only to the bottom portion 800 and the surrounding tissue together via sutures to prevent unwanted movement/rotation of the device (e.g., as illustrated with respect to FIG. 2D). In some cases, the at least one hollow male member 704 is only one hollow male member and the at least one female member 804 is only one female member, and the only one hollow male member is shaped to fit the dimensions of the only on female member.

As can be seen by the various implementations illustrated herein, a top portion includes a top vascular housing for encasing a top portion of a vessel when implanted proximal to a surface of a patient's skin and one of: 1) at least one top hollow male member extending from the top vascular housing, each of the at least one top hollow male member including a slot exposing an interior surface of the at least one top hollow male member and a top aperture formed within a downward-facing coupling edge positioned proximal to a bottom surface of the top vascular housing: or 2) at least one top female aperture disposed at the downward-facing coupling edge of the top vascular housing, the at least one top female member having a top aperture for receiving an at least one bottom hollow male member of a bottom portion. A bottom portion includes a bottom vascular housing for encasing a bottom portion of the vessel when implanted distal to the surface of the patient's skin and one of: 1) at least one bottom female member disposed at an upward-facing coupling edge of the bottom vascular housing, the at least one bottom female member having a bottom aperture for receiving the at least one top hollow male member of the top portion; or 2) at least one bottom hollow male member extending from the bottom vascular housing, each of the at least one bottom hollow male member including a slot exposing an interior surface of the at least one bottom hollow male member and a bottom aperture formed within the upward-facing coupling edge positioned proximal to a top surface of the bottom vascular housing.

In addition to having at least one top hollow male member or at least one top female member, the top portion can also include at least one second hollow male member or at least one second female member. In some cases, the top portion may include at least one top hollow male member and at least one top female member at an opposing position of the top vascular housing that is opposite of a position of the top vascular housing that the at least one top hollow male member extends from. In some cases, the bottom portion may include at least one bottom hollow male member and at least one bottom female member at an opposing position of the bottom vascular housing that is opposite of a position of the bottom vascular housing that the at least one bottom hollow male member extends from. It should be understood that, in cases in which the top portion includes at least one top hollow male member, the bottom portion includes at least one bottom female member for receiving the least one top hollow male member of the top portion and that in cases in which the bottom portion includes at least one bottom hollow male member, the top portion includes at least one top female member for receiving the at least one bottom hollow male member of the bottom portion.

Furthermore, while the vascular access device has been described in terms of over/under and/or top and bottom portions (e.g., vertically), implementations can instead include side-by-side combinations and/or left and right portions (e.g., horizontally) so that the vascular access device prevents movement/rotation in vertical and longitudinal directions/axes and prevents rotation around the horizontal axis while allowing left and right portions of the vascular access device to move linearly in the horizontal direction (e.g., when an interventional radiologist performs an angioplasty on the portion of the vessel that is encased by the vascular access device). This is accomplished with at least one hollow male member and at least one hollow female member positioned to be inserted/receive one another in a horizontal direction. Therefore, when top and bottom portions are described throughout this specification, it should be understood that left and right portions can be used in lieu of top and bottom portions and also include similar features as the left and right portions. Similarly, instead of over/under and/or top and bottom portions, the at least one hollow male member and at least one hollow female member can be positioned to be inserted/receive one another in any direction around/perpendicular to the longitudinal axis. In other words, the at least one hollow male member and at least one hollow female member can be positioned to be inserted/receive one another in any direction/angle between an over/under combination and a side-by-side combination of portions of a vascular access device.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. A vascular access device with vessel accommodation, comprising:
    a top portion comprising a vascular access aperture and at least one male/female member; and
    a bottom portion comprising at least one mating member corresponding to the at least one male/female member of the top portion that allows for controlled movement of the top and bottom portion to accommodate enlarging vessels,
    wherein the top portion further comprises a top vascular housing for encasing a top portion of a vessel when implanted proximal to a surface of a patient's skin, wherein the vascular access aperture is disposed within the top vascular housing,
    wherein the bottom portion further comprises a bottom vascular housing for encasing a bottom portion of the vessel when implanted distal to the surface of the patient's skin,
    wherein a diameter of an interior surface of the top vascular housing increases from a center of the top vascular housing to an outer longitudinal edge of the top vascular housing, wherein a diameter of an interior surface of the bottom vascular housing increases from a center of the bottom vascular housing to an outer longitudinal edge of the bottom vascular housing.

2. The vascular access device of claim 1, wherein coupling of the at least one mating member with the at least one male/female member allows for vertical movement of the top portion and the bottom portion to accommodate enlarging vessels.

3. The vascular access device of claim 1, wherein a complete vascular housing comprising a variable cross-sectional area is formed when the at least one mating member and the at least one male/female member are coupled together to accommodate enlarging vessels.

4. The vascular access device of claim 1, wherein the at least one male/female member is at least one male member and the at least one mating member is at least one female member, wherein the male member comprises a hook that, upon receipt of the male member by the female member, prevents, via a bottom aperture of the female member, decoupling of the male member from the female member.

5. The vascular access device of claim 1, wherein the at least one male/female member is at least one male member and the at least one mating member is at least one female member, wherein a shape of the male member of the top portion matches a shape of the female member of the bottom portion so that when the top portion and the bottom portion are coupled together around the vessel and affixed to tissue surrounding the vessel, linear movement in a horizontal and longitudinal direction and rotational movement around horizontal, longitudinal, and vertical axes is prevented.

6. The vascular access device of claim 1, wherein the at least one male/female member is at least one female member and the at least one mating member is at least one male member, wherein a shape of the at least one female member of the top portion matches a shape of the at least one male member of the bottom portion so that when the top portion and the bottom portion are coupled together around the vessel and affixed to tissue surrounding the vessel, linear movement in a horizontal and longitudinal direction and rotational movement around horizontal, longitudinal, and vertical axes is prevented.

7. The vascular access device of claim 1, further comprising a hinge coupling a side of the top portion and a side the bottom portion together, wherein the at least one male/female member is on an opposing side of the top portion that is opposite of the side of the top portion that is coupled to the side of the bottom portion by the hinge.

8. A vascular access device with vessel accommodation, comprising:
    a top portion comprising a vascular access aperture and at least one male/female member; and
    a bottom portion comprising at least one mating member corresponding to the at least one male/female member of the top portion that allows for controlled movement of the top and bottom portion to accommodate enlarging vessels,
    wherein the top portion further comprises a top vascular housing for encasing a top portion of a vessel when implanted proximal to a surface of a patient's skin, wherein the vascular access aperture is disposed within the top vascular housing,
    wherein the bottom portion further comprises a bottom vascular housing for encasing a bottom portion of the vessel when implanted distal to the surface of the patient's skin,
    wherein the at least one male/female member is at least one male member and the at least one mating member is at least one female member,
    wherein the at least one male member is at least one hollow male member that extends from a side of the top vascular housing.

9. The vascular access device of claim 8, wherein each of the at least one hollow male member comprises:
    a slot exposing an interior surface of the at least one hollow male member; and
    a top aperture formed within a downward-facing coupling edge positioned proximal to a bottom surface of the top vascular housing.

10. The vascular access device of claim 9, wherein the at least one female member is disposed at an upward-facing coupling edge of the bottom vascular housing, the at least one female member having a bottom aperture for receiving the at least one hollow male member of the top portion, wherein the top portion and the bottom portion are not monolithic with one another.

11. The vascular access device of claim 10, wherein the top portion further comprises at least one second male/female member on an opposing side of the top vascular housing that is opposite of the side of the top vascular housing that the at least one hollow male member extends from and the bottom portion further comprises at least one second mating member corresponding to the at least one second male/female member that allows for controlled movement of the top and bottom portion to accommodate the vessel becoming enlarged.

12. The vascular access device of claim 11, wherein the at least one second male/female member is at least one second male member and the at least one second mating member is at least one second female member.

13. The vascular access device of claim 12, wherein the at least one second male member is at least one second hollow male member that extends from the opposing side of the top vascular housing, each of the at least one second hollow male member comprising:

a second slot exposing a second interior surface of the at least one second hollow male member; and a second top aperture formed within a second downward-facing coupling edge positioned proximal to a second bottom surface of the top vascular housing;

wherein the at least one second female member is disposed at a second upward-facing coupling edge of the bottom vascular housing, the at least one second female member having a second bottom aperture for receiving the at least one second hollow male member.

14. The vascular access device of claim 11, wherein the at least one second male/female member is at least one second female member and the at least one second mating member is at least one second male member.

15. The vascular access device of claim 14, wherein the at least one second male member is at least one second hollow male member, each of the at least one second hollow male member comprising:

a second slot exposing a second interior surface of the at least one second hollow male member; and a second bottom aperture formed within a second upward-facing coupling edge positioned proximal to a top surface of the bottom vascular housing, wherein the at least one second hollow male member extends from an opposing side of the bottom vascular housing that is opposite of a side of the upward-facing coupling edge of the bottom vascular housing that the at least one second female member is disposed;

wherein the at least one second female member is disposed at a second downward-facing coupling edge of the top vascular housing, the at least one second female member having a second top aperture for receiving the at least one second hollow male member.

16. A method of using the vascular access device of claim 10, wherein the top portion and the bottom portion are secured to one another with a suture thread by:

inserting the suture thread through the bottom aperture of the at least one bottom female member and the top aperture of the at least one top hollow male member; and fastening the suture thread around the upward-facing coupling edge of the bottom vascular housing and the downward-facing coupling edge of the at least one top hollow male member.

17. The method of using the vascular access device of claim 16, wherein fastening the suture thread around the upward-facing coupling edge of the bottom vascular housing and the downward-facing coupling edge of the at least one top hollow male member comprises:

pulling excess suture thread, via the slot, from the interior surface of the at least one top hollow male member until the suture thread is taut to the upward-facing coupling edge of the bottom vascular housing and the downward-facing coupling edge of the at least one top hollow male member; and tying a surgical knot with two ends of the suture thread.

18. The method of using the vascular access device of claim 16, wherein the suture thread is biodegradable.

19. The method of using the vascular access device of claim 16, wherein sometime after the suture thread fastened, performing an angioplasty on the vessel causing the top portion and/or bottom portion to move with respect to one another in a vertical direction.

20. A vascular access device with vessel accommodation, comprising:

a top portion comprising a vascular access aperture and at least one male/female member; and a bottom portion comprising at least one mating member corresponding to the at least one male/female member of the top portion that allows for controlled movement of the top and bottom portion to accommodate enlarging vessels, wherein the top portion further comprises a top vascular housing for encasing a top portion of a vessel when implanted proximal to a surface of a patient's skin, wherein the vascular access aperture is disposed within the top vascular housing, wherein the bottom portion further comprises a bottom vascular housing for encasing a bottom portion of the vessel when implanted distal to the surface of the patient's skin, wherein the at least one male/female member is at least one female member and the at least one mating member is at least one male member, wherein the at least one male member is at least one hollow male member that extends from a side of the bottom vascular housing.

21. The vascular access device of claim 20, wherein each of the at least one hollow male member comprises:

a slot exposing an interior surface of the at least one hollow male member; and a bottom aperture formed within an upward-facing coupling edge positioned proximal to a top surface of the bottom vascular housing.

22. The vascular access device of claim 21, wherein the at least one female member is disposed at a downward-facing coupling edge of the top vascular housing, the at least one female member having a top aperture for receiving the at least one hollow male member of the bottom portion.

23. The vascular access device of claim 22, wherein the bottom portion further comprises at least one second male member extending from an opposing side of the bottom vascular housing that is opposite of the side of the bottom vascular housing that the at least one hollow male member extends from and the top portion comprises at least one second female member corresponding to the at least one second male member that allows for controlled movement of the top and bottom portion to accommodate the vessel becoming enlarged.

24. The vascular access device of claim 23, wherein the at least one second male member is at least one second hollow male member that extends from the opposing side of the bottom vascular housing, each of the at least one second hollow male member comprising:

a second slot exposing a second interior surface of the at least one second hollow male member; and a second top aperture formed within a second upward-facing coupling edge positioned proximal to a second top surface of the bottom vascular housing;

wherein the at least one second female member is disposed at a second downward-facing coupling edge of the top vascular housing, the at least one second female member having a second top aperture for receiving the at least one second hollow male member.

25. A method of using the vascular access device of claim 22, wherein the top portion and the bottom portion are secured to one another with a suture thread by:

inserting the suture thread through the top aperture of the at least one top female member and the bottom aperture of the at least one bottom hollow male member; and fastening the suture thread around the downward-facing coupling edge of the top vascular housing and the upward-facing coupling edge of the at least one bottom hollow male member.

26. The method of using the vascular access device of claim 25, wherein fastening the suture thread around the downward-facing coupling edge of the top vascular housing and the upward-facing coupling edge of the at least one bottom hollow male member comprises:

pulling excess suture thread, via the slot, from the interior surface of the at least one bottom hollow male member until the suture thread is taut to the downward-facing coupling edge of the top vascular housing and the upward-facing coupling edge of the at least one bottom hollow male member; and tying a surgical knot with two ends of the suture thread.

27. The method of using the vascular access device of claim 25, wherein the suture thread is biodegradable.

28. The method of using the vascular access device of claim 25, wherein sometime after the suture thread is fastened, performing an angioplasty on the vessel causing the top portion and/or bottom portion to move with respect to one another in a vertical direction.

29. A vascular access device with vessel accommodation, comprising:

a top portion comprising a vascular access aperture and at least one male/female member; and a bottom portion comprising at least one mating member corresponding to the at least one male/female member of the top portion that allows for controlled movement of the top and bottom portion to accommodate enlarging vessels, wherein the top portion further comprises a top vascular housing for encasing a top portion of a vessel when implanted proximal to a surface of a patient's skin, wherein the vascular access aperture is disposed within the top vascular housing, wherein the bottom portion further comprises a bottom vascular housing for encasing a bottom portion of the vessel when implanted distal to the surface of the patient's skin, wherein the at least one male/female member is at least one female member and the at least one mating member is at least one male member, wherein the at least one male member comprises a hook that, upon receipt of the at least one male member by the at least one female member, prevents, via a bottom aperture of the at least one female member, decoupling of the at least one male member from the at least one female member.

\* \* \* \* \*